United States Patent
Leclercq

(10) Patent No.: US 6,419,707 B1
(45) Date of Patent: Jul. 16, 2002

(54) ARTIFICIAL KNEE WITH ROTATABLE MENISCUS

(75) Inventor: Vincent Leclercq, Winterthur (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/633,579

(22) Filed: Aug. 7, 2000

(30) Foreign Application Priority Data

Aug. 10, 1999 (EP) .............................................. 99810719

(51) Int. Cl.$^7$ ................................................ A61F 2/38
(52) U.S. Cl. .................................. 623/20.33; 623/20.32
(58) Field of Search ........................... 623/20.32, 20.33, 623/20.34, 20.26, 20.14, 20.15

(56) References Cited

U.S. PATENT DOCUMENTS

| | | | | |
|---|---|---|---|---|
| 3,837,009 A | * | 9/1974 | Walker ................................ | 3/1 |
| 4,714,474 A | * | 12/1987 | Brooks, Jr. et al. ............ | 623/20 |
| 5,871,543 A | * | 2/1999 | Hofmann ...................... | 623/20 |
| 5,928,286 A | * | 7/1999 | Ashby et al. .................. | 623/20 |
| 6,090,144 A | * | 7/2000 | Leto et al. ..................... | 623/20 |
| 6,123,728 A | * | 9/2000 | Brosnahan et al. ...... | 623/20.24 |
| 6,210,443 B1 | * | 4/2001 | Marceaux et al. ........ | 623/20.33 |

FOREIGN PATENT DOCUMENTS

EP 0529408 A1 3/1993

* cited by examiner

*Primary Examiner*—David J. Isabella
*Assistant Examiner*—Urmi Chattopadhyay
(74) *Attorney, Agent, or Firm*—Townsend and Townsend and Crew LLP

(57) ABSTRACT

An artificial knee joint has a meniscus part (1) which is displaceably journalled on a tibia platform (2) and a guiding part (7) which is rotatably journalled on the tibia platform (2) and which engages into a guide (8) of the meniscus part (1), with the guiding part and the meniscus part having lateral guiding surfaces (9a, 10a; 9b, 10b) for guiding the meniscus part (1). In order to limit the surface pressure between the guiding surfaces (9a, 9b; 10a, 10b) the lateral guiding surfaces (9a, 9b; 10a, 10b) have different radii of curvature ($R_1$, $R_2$) which are greater than 10 cm, with the sum of the reciprocals of the radii of curvature $1/R_1 + 1/R_2$ being less than $0.2$ cm$^{-1}$.

11 Claims, 3 Drawing Sheets

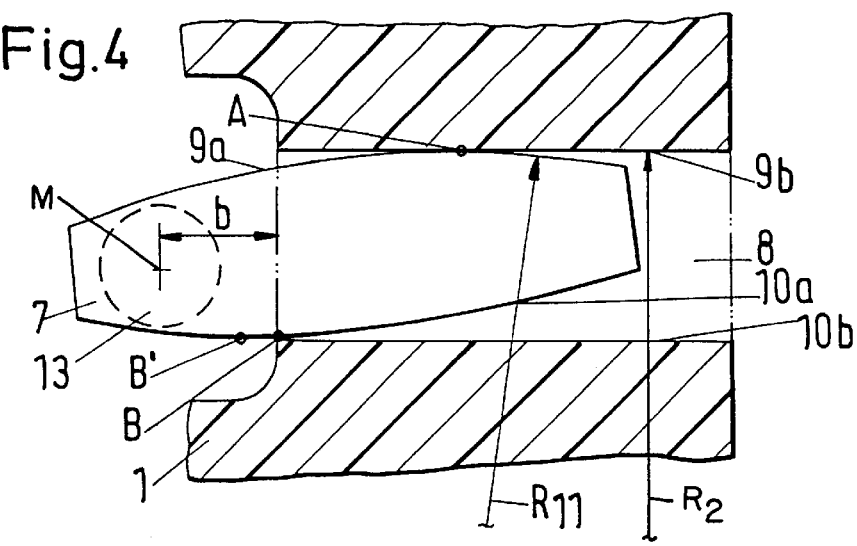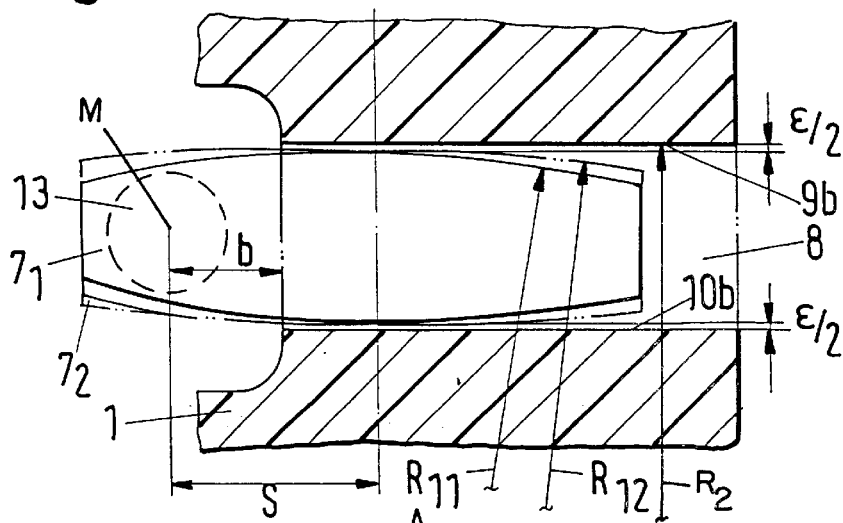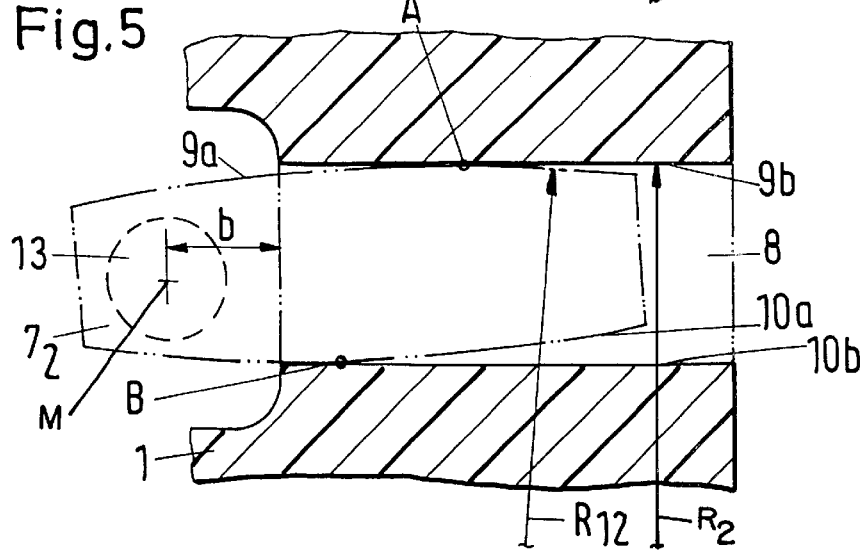

ARTIFICIAL KNEE WITH ROTATABLE MENISCUS

BACKGROUND OF THE INVENTION

The invention relates to an artificial knee joint comprising a meniscus part which is displaceably journalled on a tibia platform and comprising a guiding part which is rotatably journalled relative to the tibia platform and which engages into a guide of the meniscus part, with the guiding part and the meniscus part having lateral guiding surfaces for guiding the meniscus part.

EP-A-0 529 408 discloses a meniscus part journalled on a tibia platform and guided by a rotatable guiding part. In this a rectilinear longitudinal guiding arises through parallel guiding surfaces of the guiding part and the meniscus part, onto which the rotation of the guiding part can be superimposed. It is usual to manufacture the contacting guiding surfaces of different materials such as for example polyethylene and metal in order to produce favorable sliding pairings. In plastics such as polyethylene it must be observed that the specific pressure forces do not become too large in order to prevent cold flow and abrasion.

In knee prostheses of the above-named kind the greatest lateral forces to be transmitted between the guiding part and the meniscus part arise in the extended position, in which the meniscus part assumes a forward position on the tibia platform. Only in this approximately extended position can a prosthesis wearer carry heavy loads analogously to the natural joint, push itself laterally away or receive blows which are not resiliently taken up by muscles and bands. At the same time, in its most forward position the meniscus part is at the greatest distance from the point of rotation of the guiding part, so that unfavorable conditions for a lateral force transmission can arise.

SUMMARY OF THE INVENTION

It is an object of the invention to provide guiding systems with a guiding part and meniscus in which excessive surface pressures under lateral forces are avoided. This object is satisfied in that the lateral guiding surfaces of the guiding part and the associated guiding surfaces of the meniscus part have different radii of curvature $R_1$, $R_2$ which are greater than 10 cm, with the sum of the reciprocals $1/R_1+1/R_2$ being less than 0.2 cm$^{-1}$.

An advantage of the invention consists in that the point of rotation M for the guiding part can constructionally be placed relatively far towards the posterior in the direction of the cross bands which are present at the natural joint without impermissible tension peaks arising on account of this in the event of lateral forces.

Since contact points A, B between the guiding part and the meniscus part are provided with radii of curvature of more than 10 cm in the guiding direction, all possible curvature combinations yield a more favorable value than a constellation such as is for example shown in FIG. 1 as prior art.

The influence of the curvature can be shown using the example of spherical surfaces with sphere diameters $D_1$, $D_2$. If at a support point only the diameter of the sphere surface is changed, the maximum surface pressure is a) in the case of a "sphere with diameter D on a planar surface" proportional to $$\sqrt[3]{\frac{1}{D^2}}$$

b) in the case of "sphere $D_2$ against sphere $D_1$" proportional to $$\sqrt[3]{\frac{1}{\left(\frac{D1 \times D2}{D1+D2}\right)^2}}$$

c) in the case of "sphere $D_2$ against larger spherical shell $D_1$" proportional to $$\sqrt[3]{\frac{1}{\left(\frac{D1 \times D2}{D1-D2}\right)^2}}$$

If a theoretical comparison is made on this basis, there results for a sphere with a diameter of 1 cm which corresponds approximately to the width of a guiding part, in case a) a value of 1, in comparison with which stand a value of 0.13 with a sphere of 20 cm, and in case c) a value of 0.126 with a sphere of 20 cm against a shell of 200 cm diameter, which would correspond to an improvement by a factor of 7. Even in case b) two spherical surfaces with diameter 20 cm and 200 cm would still yield a value of 0.14, which corresponds to an improvement by a factor of 6.9.

From the point of view of the surface pressure, radii of curvature which are as large as possible are advantageous. In practice, however, limits are set in that the contact points must lie in the region of the overlapping guiding surfaces. The larger the radii of curvature are, the greater is the influence of the manufacturing tolerances and of the clearance between the guiding part and the meniscus on the contact points A, B still being located within the overlapping guiding surfaces with predetermined radii of curvature. For manufacturing reasons therefore those solutions are advantageous in which the guiding surfaces can be manufactured simply and within narrow tolerances, since the clearance depends on the precision with which the guiding surfaces of the meniscus lie at a predetermined distance from one another and the guiding surfaces of the guiding part lie at a predetermined distance from one another. With higher precision of the predetermined distances the smaller of the radii of curvature $R_1$, $R_2$ can take on values greater than 20 cm, and the sum of the reciprocal values of the radii of curvature $1/R_1+1/R_2$ can be less than 0.1 cm$^{-1}$. With very high precision of the predetermined distances the smaller of the radii of curvature $R_1$, $R_2$ can take on values greater than 30 cm, and the sum of the reciprocal values of the radii of curvature $1/R_1+1/R_2$ can be less than 0.067 cm$^{-1}$. In this consideration, planar guiding surfaces are associated with infinitely large radii of curvature.

An embodiment which is more simple in manufacturing technique results with a meniscus part of which the guiding surfaces extend straight and parallel to one another and a guiding part with convex guiding surfaces. Instead of straight, the guiding surfaces of the meniscus part can also extend slightly concavely with a substantially greater radius of curvature than that of the guiding part.

A further embodiment, which is considered more difficult in manufacturing technique, has a guiding part with guiding surfaces that extend straight and parallel to one another and a meniscus part that has convex guiding surfaces. Instead of straight, the guiding surfaces of the guiding part can also extend slightly concavely with a substantially greater radius of curvature than that of the meniscus part.

BRIEF DESCRIPTION OF THE DRAWINGS

FIG. 3 is a plan view of an arrangement with two convex guiding parts having different radii of curvature, with the meniscus part being located in the forward, i.e. anterior, position and a similar clearance ∈/2 being present between the guiding surfaces.

FIG. 4 shows the arrangement of FIG. 3 with the smaller radius of curvature $R_{11}$ of the convex guiding surfaces of the guiding part.

FIG. 5 shows the arrangement of FIG. 3 with the larger radius of curvature $R_{12}$ of the convex guiding surfaces of the guiding part.

DESCRIPTION OF THE PREFERRED EMBODIMENTS

In the examples, arrangements at an artificial knee joint are shown comprising a meniscus part which is displaceably journalled on a tibia platform and comprising a guiding part which is rotatably journalled on the tibia platform and which engages into a guide of the meniscus part, with the guiding part and the meniscus part having lateral guiding surfaces (9a, 10a; 9b, 10b). In order to limit the surface pressure between the guiding surfaces, the guiding surfaces have different radii of curvature $R_1$, $R_2$ with amounts which are greater than 10 cm, and the sum of the reciprocals of the radii of curvature $1/R_1 + 1/R_2$ is less than 0.2 cm$^{-1}$.

Figure 1:
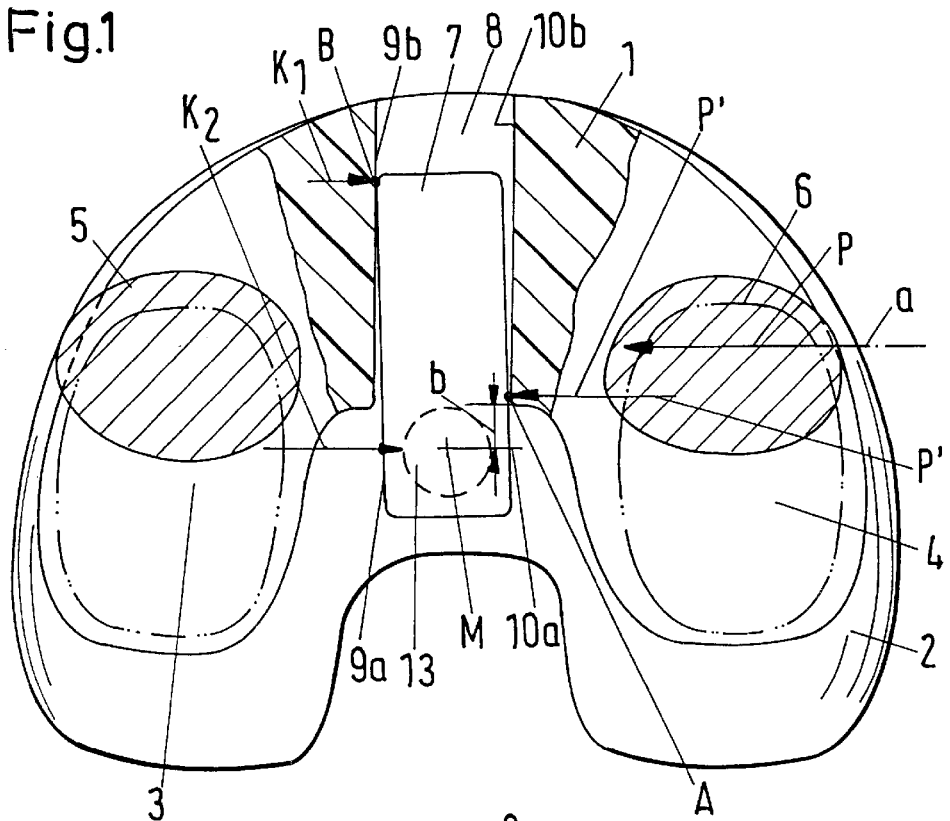
FIG. 1 is a plan view of a prior art tibia platform with a guiding part and meniscus.

On the basis of the illustration of FIG. 1 the problems of the lateral forces at a conventional arrangement will be shown first. A guiding part 7 with straight parallel guiding surfaces 9a, 10a is journalled with a pin 13 on a tibia platform 2 and is rotatable about a point of rotation M. The condyles 5, 6, which are recognizable only in section, are journalled in bearing shells 3, 4 of the meniscus part and experience a lateral force P in a line of action a, which they transmit to the meniscus part 1, which in turn passes this lateral force on to the guiding part 7. The likewise straight and parallel guiding surfaces 9b, 10b now act on the guiding part in order to achieve a state of equilibrium, with it being possible for the guiding part to rotate within the framework of the clearance of the lateral guides 9a, 9b, 10a, 10b until there arise at a contact point A a lateral force P', which is reduced up to there, and at a contact point B a reaction force $K_1$ as well as at the pin 13 a reaction force $K_2$. Corresponding to the radii of curvature of the guiding surfaces which are present at the contact points A and B there result surface pressures which, depending on the material combination, e.g. polyethylene against metal, can lead to an undesirably large wear, with it being less a matter of an enlargement of the clearance than of the arising of wear particles and their remaining in the human body which is undesirable.

The position of the meniscus part 1 shown in FIG. 1 corresponds to the most forward anterior position on the tibia platform. In this position the overlapping region of the guiding surfaces 9a, 9b and the guiding surfaces 10a, 10b is displaced to the anterior by a distance b from the point of rotation M of the pin 13, and a torque P'·b arises which determines the reaction force K1 at the point B. Unfortunately the greatest lateral forces arise in the approximately extended position of the knee joint so that in this position large lateral forces and small radii of curvature coincide at the contact points A and B. To make matters worse, in this position the guiding part 7 must not project towards the anterior as far as the meniscus part 1, in order that in the posterior position of the meniscus part no larger shoulders of the guiding part project towards the anterior beyond the meniscus part which could injure tissue parts in a rotation of the meniscus part. In the following exemplary embodiments in accordance with the invention the same reference symbols as in FIG. 1 will be used. They differ with respect to their geometry through the design of the lateral guides 9a, 9b and 10a, 10b.

Figure 2:
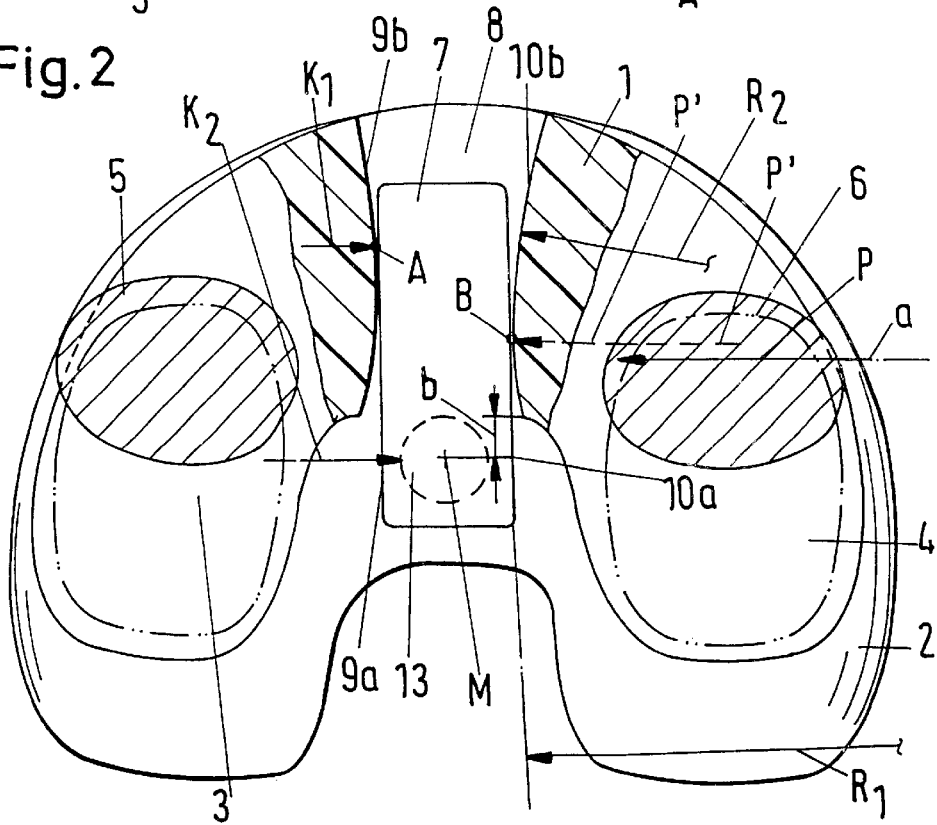
FIG. 2 is a plan view of an arrangement made in accordance with the invention with concave guiding surfaces at the guiding part and with convex guiding surfaces at the meniscus part.

In the example of FIG. 2 the meniscus part 1 is illustrated in its anterior position. In a numerical example the distance b from the beginning of the guiding surfaces 9b, 10b to the point of rotation M of the guiding part 7 amounts to 0.542 cm. The shortest distance between the guiding surfaces 9b, 10b of the meniscus part amounts to 1.35 cm. The lateral guiding surfaces 9b, 10b of the meniscus part 1 are convexly curved and have a radius of curvature $R_2$. The lateral guiding surfaces 9a, 10a of the guiding part 7 are slightly concavely arched and have a radius of curvature $R_1$ which is substantially greater than the radius of curvature $R_2$. In the numerical example $R_2$ amounts to 32.0 cm; $R_1$=100.0 cm and the straight connecting line of the centers for the radii of curvature $R_2$ represents at the same time a bisector and a symmetry axis for the guiding surfaces 9b, 10b of the meniscus part 1, whereas the straight connecting line of the centers for the radii of curvature $R_1$ represents at the same time a bisector and a symmetry axis for the guiding surfaces 9a, 10a of the guiding part. The total clearance is dimensioned to be so large that during the displacement towards the posterior of the meniscus part no jamming takes place. The larger the radius of curvature $R_1$ is, the lower is the danger of a binding. And with planar and parallel guiding surfaces 9a, 10a, to which an infinitely large radius of curvature corresponds, no binding can take place any longer, so that the clearance between the guiding part and the guide can be chosen to be particularly small. The guide 8 is formed in the following cases as a groove. It could in principle also be formed as an elongate hole. The clearance between the guiding part and the guide together with the magnitude of the radii of curvature $R_1$, $R_2$ and the position of the centers with respect to R1 and $R_2$ which is kept in the longitudinal direction with respect to the associated guiding surfaces determine the location of the contact points A and B within the overlapping of the guiding surfaces 9a, 9b and 10a, 10b. In this way one has the possibility of choosing the position of the contact points A, B and large radii of curvature R1, $R_2$ in order to arrive at lower surface pressings. The slight rotation of the guiding part 7 with respect to the meniscus part 1 has as a result a slight transverse displacement of the meniscus part on the tibia platform 2, which is not considered significant. In the numerical example there results in the anterior position of the meniscus part a distance of 1.314 cm in the longitudinal direction between the points A and B and a rotation of the guiding part 1 by 1.3°.

In FIGS. 3 and 5 a further arrangement with a guiding part $7_2$ having convex guiding surfaces and with a meniscus part 1 having straight, parallel guiding surfaces 9b, 10b is shown. Strictly taken, two guiding parts $7_1$ and $7_2$ are shown in FIG. 3 which—in order to provide a numerical example—uniformly subdivide a same total clearance $\epsilon=0.02$ from the guiding surfaces 9b, 10b in the neutral middle position. The guiding parts have a length of 2.75 cm and a largest width of 1.33 cm. The centers of the radii of curvature $R_1$ lie on the bisector of the guiding part in the transverse direction. This bisector is displaced towards the anterior by the amount s=0.778 cm from the point of rotation M of the guiding part. The guiding surfaces 9b, 10b of the meniscus part end at a distance b=0.5 cm ahead of the point of rotation M of the guiding part.

The guiding part $7_1$ has a radius of curvature $R_{11}=10.0$ cm of the guiding surfaces, which is dimensioned too small for the clearance $\epsilon=0.02$ cm and, as is indicated in FIG. 4, leads to the edge of the meniscus part determining the contact point B, whereas a theoretical contact point B' with radius of curvature $R_{11}$ lies against a straight line outside the overlapping of the guiding surfaces 10a, 10b of the guiding part and the meniscus part. A correction possibility in order to reduce the inclined position of the guiding part of initially 3° here and to bring the contact points into the overlapping of the guides consists in the reduction of the clearance $\epsilon$. Another correction possibility is the enlargement of the radius of curvature $R_{11}$.

In FIG. 5 the arrangement with the guiding part $7_2$ is shown of which the guiding surfaces 9a, 10a are provided with a radius of curvature $R_{12}$, which leads to a contact point B within the overlapping of the guiding surfaces 10a, 10b in an arrangement which is otherwise the same. For the above numerical example, in relation to FIG. 3, such a situation with a radius $R_{12}=32.0$ cm, the center of which is displaced towards the anterior by an amount s=0.778 cm from the point of rotation M of the pin, can be achieved with a guiding part of length 2.75 cm, with a length of the guiding surfaces 9b, 10b of the meniscus part of 1.8 cm, with a distance of the overlapping from the point of rotation M of b=0.5 cm and with a clearance of $\epsilon=0.02$ cm. The inclined position of the guiding part amounts only to about 1.7°. It is evident that the manufacturing tolerances for the guiding surfaces 9a, 10a and 9b, 10b must be contained in this clearance of $\epsilon=0.02$ cm in order that a situation as in FIG. 4 does not arise.

Figure 6:
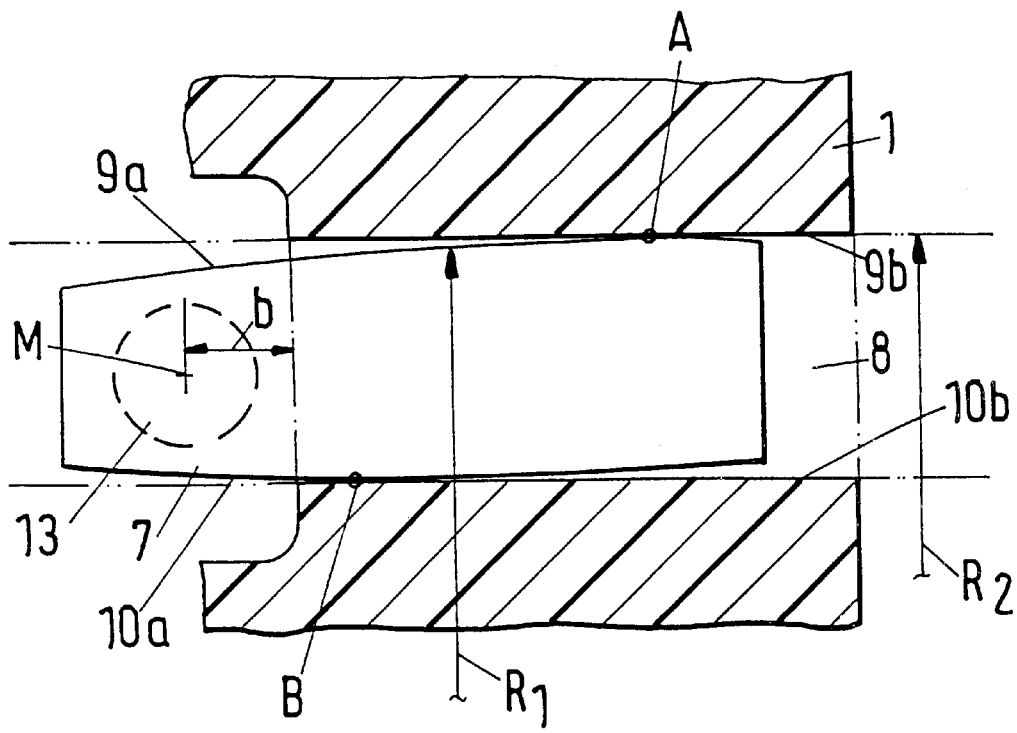
FIG. 6 shows an arrangement with convex guiding surfaces of the guiding part and with concave guiding surfaces of the meniscus part.

In the example of FIG. 6 the guiding surfaces 9b, 10b of the meniscus part are no longer parallel and straight in comparison with FIG. 5, but rather very slightly concavely curved. The centers of the radii of curvature R1 of the meniscus part lie transverse to the guiding surfaces 9b, 10b on their middle line in the transverse direction. In order to remain with the numerical values of the example pertaining to FIG. 5, a radius of curvature $R_2=100.0$ cm and a narrowest distance of 1.35 cm between the guiding surfaces 9b, 10b of the meniscus part 1 at the beginning of the guiding surfaces would suffice in order to obtain contact points A and B within the overlapping and to maintain them within the overlapping until their distance b from the point of rotation M has reduced to zero.

Figure 7:
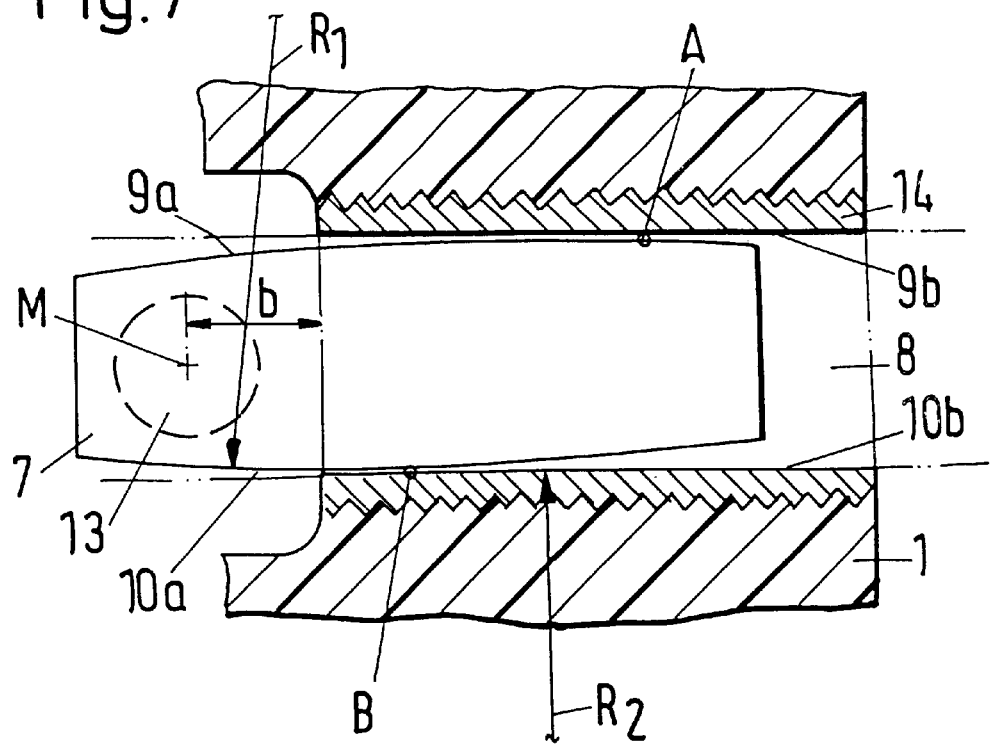
FIG. 7 shows an arrangement with convex guiding surfaces of the guiding part and with convex guiding surfaces of the meniscus part.

In the example of FIG. 7 the guiding surfaces 9b, 10b of the meniscus part 1 are no longer parallel and straight in comparison with FIG. 5, but rather very slightly convexly curved. Here as well it is possible with a very large radius of curvature $R_2$ of for example 100.0 cm to perform a displacement out of the anterior position by an amount b without this radius of curvature $R_2$ on the meniscus part 1 being departed from by contact point B or A. In this last exemplary embodiment, however, particularly high demands are placed on the clearance or on the manufacturing tolerances which are to be observed respectively. In a guiding part of the numerical example pertaining to FIG. 5 and with a shortest distance of 1.35 cm between the guiding surfaces 9b, 10b at their bisector, there results an inclined position of the guiding part in the anterior position of the meniscus part of 1.8° and there arise contact points A, B within the overlapping of the guiding surfaces 9a, 9b and 10a, 10b.

In order to keep the manufacturing tolerances of a guide groove 8 in general low in a plastic such as for example polyethylene, it can be advantageous to manufacture this groove in an insertion piece 14 of metal and to anchor the latter in the meniscus part 1, as is shown in FIG. 7. A groove of this kind has the advantage that it substantially changes the distance of its guiding surfaces 9b, 10b neither through swelling nor through temperature fluctuations.

A further aspect is the multiple use of a guiding part $7_2$, such as is shown in FIG. 5, for meniscus parts 1 of different sizes and for tibia platforms 2 of different sizes in order to be able to use one guiding part for different knee sizes. In an insert of this kind it can happen that not all combinations with different meniscus parts produce a distance b of their guidings 9b, 10b from the point of rotation M of the guiding part in the anterior position, which leads to the skewing of the guiding part. In spite of this it is advantageous for the parts economy also to cover those cases in which no skewing arises for example with a "universal guiding part" having convex guiding surfaces 9a, 10a and having straight parallel guiding surfaces 9b, 10b of the meniscus part 1.

I claim:

1. Artificial knee joint comprising a meniscus part displaceably journalled on a tibia platform and comprising a guiding part which is rotatably journalled relative to the tibia platform and which engages into a guide of the meniscus part, the guiding part and the meniscus part having lateral guiding surfaces for guiding the meniscus part, the lateral guiding surfaces of the guiding part and the associated guiding surfaces of the meniscus part having different radii of curvature which are greater than 10 cm, the sum of the reciprocals of the radii of curvature being less than 0.2 cm$^{-1}$.

2. Artificial knee joint in accordance with claim 1 wherein the radii of curvature are greater than 20 cm, with the sum of the reciprocals of the radii of curvature being less than 0.1 cm$^{-1}$.

3. Artificial knee joint in accordance with claim 1 wherein the radii of curvature are greater than 30 cm, the sum of the reciprocals of the radii of curvature being less than 0.067 cm$^{-1}$.

4. Artificial knee joint in accordance with claim 1 wherein the guiding surfaces of the guiding part are convex and the guiding surfaces of the meniscus part are concave or rectilinear.

5. Artificial knee joint in accordance with claim 1 wherein the guiding surfaces of the meniscus part are convex and the guiding surfaces of the guiding part are concave or rectilinear.

6. Artificial knee joint in accordance with claim 1 wherein the guiding surfaces of the guiding part are metallic and the guiding surfaces of the meniscus part are of plastic.

7. Artificial knee joint in accordance with claim 1 wherein the guiding surfaces of the guiding part and the meniscus part are metallic.

8. Artificial knee joint in accordance with claim 1 wherein a point of rotation of the guiding part is displaced towards the posterior in a longitudinal direction when viewed from a middle of the guiding part.

9. Artificial knee joint in accordance with claim 1 including a plurality of meniscus parts of different sizes and different lengths guiding surfaces for use with a given guiding part.

10. Artificial knee joint in accordance with claim 1 wherein the guiding part has a rotation pin which is journalled in the tibia platform.

11. Artificial knee joint comprising at least one meniscus part carried on a tibia platform and having a guiding part which is rotatable about a point of rotation relative to the tibia platform and which engages a guide of the meniscus part, the guiding part and the meniscus part having lateral guiding surfaces for guiding the meniscus part, the lateral guiding surfaces of the guiding part and the lateral guiding surfaces of the meniscus part having different radii of curvature which are greater than 10 cm, with the sum of the reciprocals of the radii of curvature being less than $0.2 \text{ cm}^{-1}$.

* * * * *